(12) United States Patent
Freeman et al.

(10) Patent No.: US 10,245,005 B2
(45) Date of Patent: Apr. 2, 2019

(54) ULTRASOUND TRANSDUCER PROBE WITH MICROBEAMFORMER FOR MULTILINE IMAGING

(71) Applicant: KONINKLIJKE PHILIPS N.V., Eindhoven (NL)

(72) Inventors: Steven Russell Freeman, Eindhoven (NL); Bernard Joseph Savord, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 721 days.

(21) Appl. No.: 14/648,741

(22) PCT Filed: Nov. 29, 2013

(86) PCT No.: PCT/IB2013/060499
§ 371 (c)(1),
(2) Date: Jun. 1, 2015

(87) PCT Pub. No.: WO2014/087306
PCT Pub. Date: Jun. 12, 2014

(65) Prior Publication Data
US 2015/0297183 A1    Oct. 22, 2015

Related U.S. Application Data

(60) Provisional application No. 61/732,519, filed on Dec. 3, 2012.

(51) Int. Cl.
*A61B 8/00* (2006.01)
*G01S 15/89* (2006.01)
(Continued)

(52) U.S. Cl.
CPC ............ *A61B 8/4494* (2013.01); *A61B 8/145* (2013.01); *A61B 8/4444* (2013.01);
(Continued)

(58) Field of Classification Search
CPC ..... A61B 8/145; A61B 8/4444; A61B 8/4494; G01S 15/8925; G01S 7/5208; G01S 15/52095; G10K 11/346
See application file for complete search history.

(56) References Cited

U.S. PATENT DOCUMENTS

| 4,644,795 A | 2/1987 | Augustine |
| 5,229,933 A | 7/1993 | Larson |

(Continued)

FOREIGN PATENT DOCUMENTS

| JP | 09322896 A | 12/1997 |
| WO | 0217296 A1 | 2/2002 |

(Continued)

*Primary Examiner* — Michael T Rozanski

(57) ABSTRACT

An array transducer probe has transducer elements arranged in adjacent patches (62, 64, 66) of groups of transducer elements. A microbeamformer in the probe is coupled to the elements of the array to transmit ultrasound beams and delay echo signals received by the transducer elements. In a standard configuration the elements of each patch (62, 64, 66) are coupled to the summing node (72, 74, 76) of that patch. The elements of each patch may also be coupled to the summing nodes of one or more adjacent patches. For multiline (4', 6') reception some of the elements of the active aperture are coupled to the summing node of one patch, and other elements of the active aperture are coupled to the summing node of another patch. This coupling provides at least two different patch signals to channels (82, 84) of a system beamformer for multiline processing.

14 Claims, 7 Drawing Sheets

(51) Int. Cl.
*A61B 8/14* (2006.01)
*G01S 7/52* (2006.01)
*G10K 11/34* (2006.01)

(52) U.S. Cl.
CPC ........ *G01S 7/5208* (2013.01); *G01S 7/52095* (2013.01); *G01S 15/8925* (2013.01); *G01S 15/8927* (2013.01); *G10K 11/346* (2013.01)

(56) References Cited

U.S. PATENT DOCUMENTS

| | | |
|---|---|---|
| 5,318,033 A | 6/1994 | Savord |
| 5,997,479 A | 12/1999 | Savord |
| 6,013,032 A | 1/2000 | Savord |
| 6,126,602 A | 10/2000 | Savord |
| 6,375,617 B1 | 4/2002 | Fraser |
| 7,537,567 B2 | 5/2009 | Jago |
| 8,177,718 B2 | 5/2012 | Savord |

FOREIGN PATENT DOCUMENTS

| | | |
|---|---|---|
| WO | 2006003621 A1 | 1/2006 |
| WO | 2007099474 A1 | 9/2007 |

ULTRASOUND TRANSDUCER PROBE WITH MICROBEAMFORMER FOR MULTILINE IMAGING

This application is the U.S. National Phase application under 35 U.S.C. § 371 of International Application No. PCT/IB2013/060499, filed on Nov. 29, 2013, which claims the benefit of U.S. Provisional Application No. 61/732,519 filed on Dec. 3, 2012. These applications are hereby incorporated by reference herein.

This invention relates to medical diagnostic ultrasound systems and, in particular, to ultrasound transducer probes with microbeamformers for multiline imaging.

Ultrasound array transducers may be configured as a single row of transducer elements, a one-dimensional (1D) array for imaging a two dimensional (2D) image plane, or as a two dimensional (2D) array of transducer element for imaging a three dimensional region. A 2D array comprises elements extending in both azimuth and elevation directions which can be operated fully independently to both focus and steer beams in any azimuth or elevation direction. These arrays can be configured in either flat or curved orientations. The present invention is directed to array transducers which use microbeamformers coupled to groups of array elements which partially beamform groups of elements for the formation of multiple receive lines in response to a single transmit event.

Two dimensional array transducers as well as 1D arrays with large numbers of elements pose a problem due to their large number of transducer elements. Since each of these elements must be individually controlled on transmit and receive, a separate signal line must be provided for each element. A 1D array may comprise a row of 100-200 elements, requiring 100-200 signal lines, which can be accommodated in a relatively small and light probe cable, but may need to operate with a system beamformer of relatively few channels. A 2D array may have 100-200 rows of elements in one dimension and 100-200 columns of elements in the other dimension, totaling thousands of individual elements. A cable of many thousands of signal lines is not practical for a probe which is hand-held and must be manipulated by the sonographer. An implementation of the present invention overcomes these problems by use of a microbeamformer integrated circuit attached to the transducer array which performs partial beamforming of groups of elements referred to as patches. The individually delayed and summed signals of each patch are conducted over a standard size cable to the ultrasound system beamformer where the summed signal from each patch is applied to a channel of the system beamformer, which completes the beamforming operation. This partitioning of the full beamforming operation between a microbeamformer in the probe and the channels of the system beamformer, is illustrated for instance in U.S. Pat. No. 5,229,933 (Larson, III), U.S. Pat. No. 5,997,479 (Savord et al.), U.S. Pat. No. 6,013,032 (Savord), and U.S. Pat. No. 6,126,602 (Savord et al.), which enables the use of a cable with a relatively few number of signal lines between the probe and the ultrasound system beamformer.

It is often desirable to receive multiple scanlines in response to a single transmit event, either to increase the frame rate of display or to increase the scanline density. Multiple receive lines can be formed from a fewer number of transmit events in several ways. One technique is to interpolate synthetic receive lines between actual receive lines as described in U.S. Pat. No. 5,318,033 (Savord). In the implementation shown in this patent, two synthetic receive lines are interpolated between each pair of actual receive lines. Another technique for multiline reception, which does not require buffering of previously received lines, is to beamform multiple lines as echoes are received from one transmit event by applying separate, different delays of the echo signals as they are received. The different delays can produce multiple different beams which are steered in different directions. One technique is to transmit one "fat" beam which insonifies multiple scanline locations as described in U.S. Pat. No. 4,644,795 (Augustine). Multiple beams are formed from echoes received along the multiple scanlines. Another technique is to simultaneously transmit multiple beams in different directions and simultaneously form receive beams in the multiple directions as described in U.S. Pat. No. 7,537,567 (Jago et al.) In both cases echoes are delayed by different delays as they are received to differently delay, then separately sum, the echoes to form multiple receive beams simultaneously.

An ultrasound probe with a microbeamformer is generally designed with a predetermined configuration that operates with a corresponding system beamformer configuration. Commercially available probes with microbeamformers have a number of microbeamformer outputs which match the number of system beamformer channels. A 64-element 1D array probe may be configured with eight patches, each of eight individual transducer elements, providing eight partially beamformed signals from the eight patch outputs that are coupled to the eight channels of an 8-channel system beamformer, for example. But a problem arises when the system beamformer is performing multiline beamforming. In that case, different system beamformer channels apply different delays to a partially beamformed signal (partial beamsum) to form differently steered multilines, e.g., one steered to the left of the center of the transmit beam and one steered to the right of the center. The problem arises because ultrasound beamforming uses an expanding aperture on receive, which starts with a small aperture for the start of reception in the near field and expands that aperture by adding additional elements to the aperture as echoes are received from increasing depths of field. Depending on the location of the transmit and receive beams, the few elements used in the near field during reception can be of the same microbeamformer patch, which is connected to only a single channel of the system beamformer. Thus, only a single delay, that of the single channel, can be applied to echoes received in the near field. As the aperture expands the added elements will eventually be those of adjacent patches coupled to different system beamformer channels, enabling different delays to be applied, and the problem diminishes. It would be desirable to always receive near field signals with the elements of multiple microbeamformer patches, regardless of the location of the beams, so that multilines can always be formed from the outset of echo reception, even from the near field.

In accordance with the principles of the present invention, an ultrasonic transducer probe utilizes an array transducer with a microbeamformer having partial beamsum patch outputs coupled to channels of a system beamformer. The elements of each patch have a standard connection in a conventional patch configuration, but can also be selectively switched to be connected to the summing node of at least one adjacent patch. This enables the elements of a conventional patch to be selectively coupled to different patches and hence to multiple separate channels of a system beamformer. The system beamformer can then form multiple receive multilines simultaneously, even in the near field.

Figure 1:
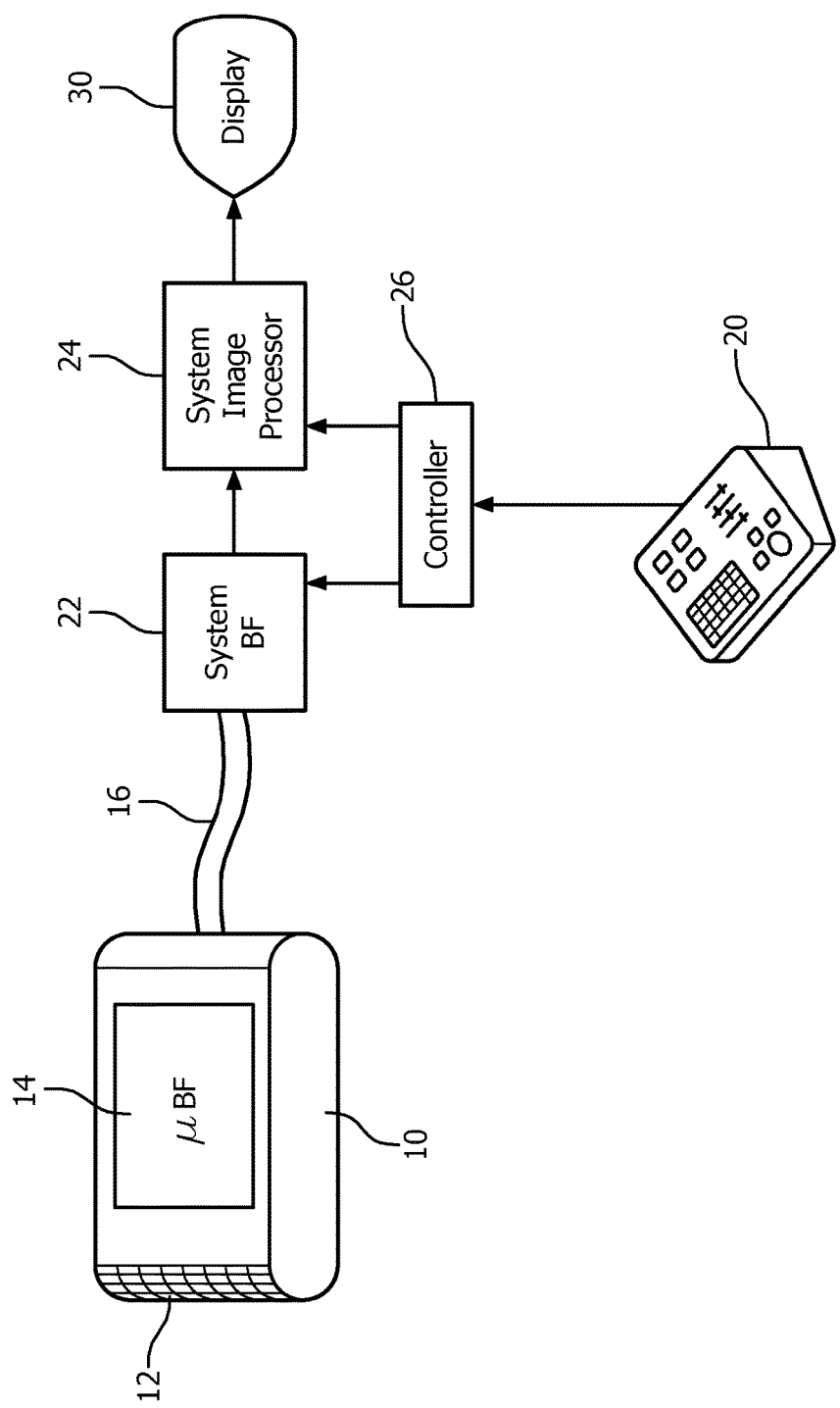
FIG. 1 illustrates in block diagram form a 2D curved array transducer and microbeamformer probe of the present invention.

Referring first to FIG. 1, an ultrasound system constructed in accordance with the principles of the present invention is shown in block diagram form. A probe 10 has a two dimensional array transducer 12 which in this example is curved in the elevation dimension such as that shown in U.S. Pat. No. 7,927,280 (Davidsen). The elements of the array are coupled to a microbeamformer 14 located in the probe behind the transducer array. The microbeamformer applies timed transmit pulses to elements of the array to transmit beams in the desired directions and to the desired focal points in the three dimensional image field in front of the array. Echoes from the transmitted beams are received by the array elements and coupled to delays of the microbeamformer 14 where they are individually delayed. The delayed signals of a group of transducer elements comprising a patch are combined to form a partial sum signal for the patch. The elements of a patch in this embodiment are operated together and have their signals individually delayed in relation to a reference and then combined by the microbeamformer to form one signal from the patch for a probe conductor or an ultrasound system beamformer channel. In a typical implementation combining is done by coupling the delayed signals from the elements of the patch to a common bus or summing node, obviating the need for summing circuits or other complex circuitry. The summing node of each patch is coupled to a conductor of a cable 16, which conducts the partial beamsum patch signal to the system mainframe. In the system mainframe the patch signals are digitized and coupled to channels of a system beamformer 22, which appropriately delays each patch signal. The delayed patch signals are then combined to form a coherent steered and focused receive beam. The beam signals from the 3D image field are processed by a system image processor 24 to produce 2D or 3D images for display on an image display 30. Control of ultrasound system parameters such as probe selection, beam steering and focusing, and signal and image processing is done under control of a controller 26 which is coupled to various modules of the system. In the case of the probe 10 some of this control information is provided to the microbeamformer from the system mainframe over data lines of the cable 16. The user controls many of these operating parameters by means of a control panel 20.

Figure 2:
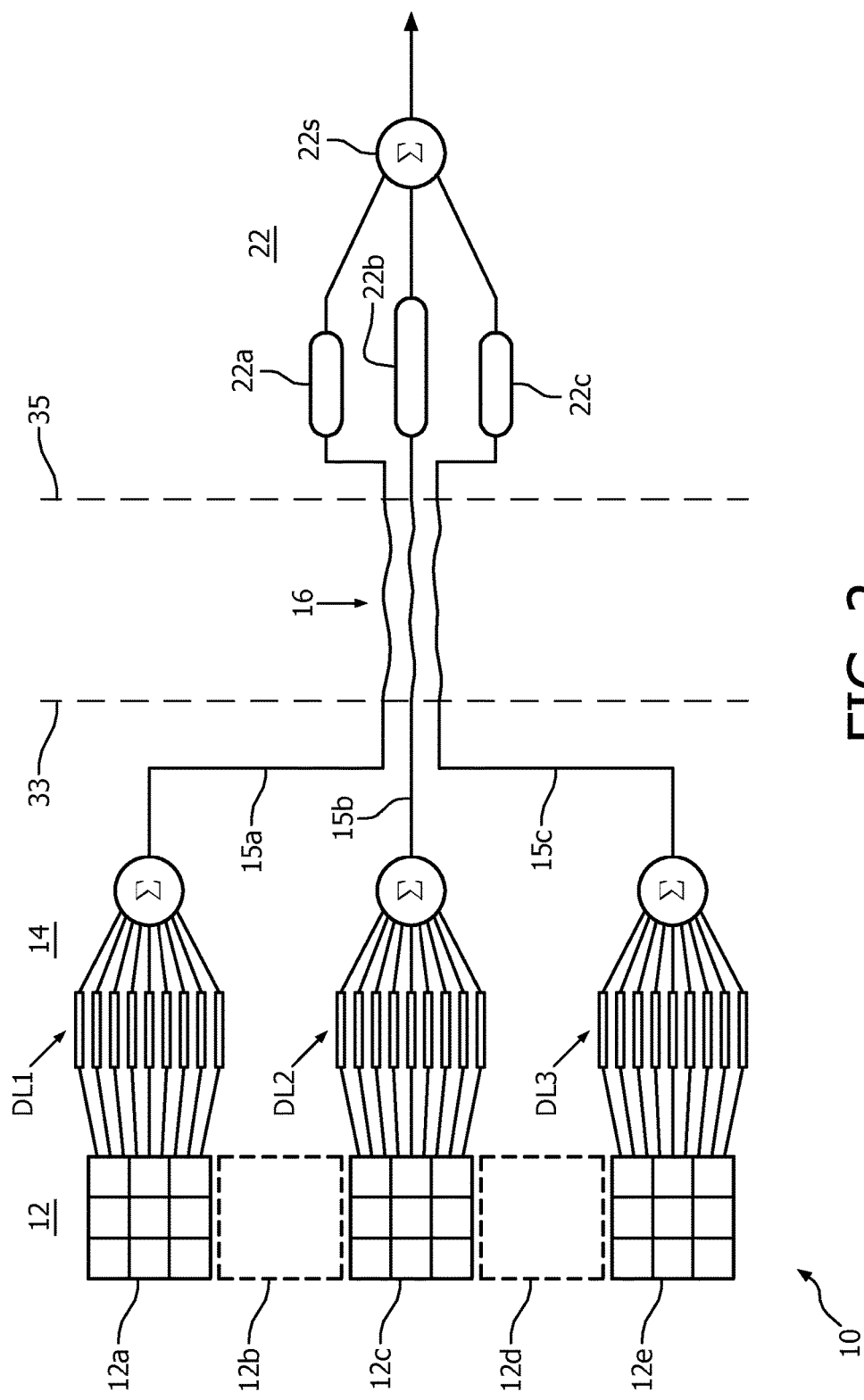
FIG. 2 is a block diagram illustrating the concept of a partial beamsum microbeamformer.

FIG. 2 illustrates the concept of a partially summing microbeamformer. The drawing of FIG. 2 is sectioned into three areas by dashed lines 33 and 35. Components of the probe 10 are shown to the left of line 33, components of the system mainframe are shown to the right of line 35, and the cable 16 is shown between the two lines. The elements of the transducer array 12 of the probe are divided into patches of contiguous transducer elements. Five of the patches of the array 12 are shown in the drawing, each including nine neighboring elements. The microbeamformer channels for patches 12a, 12c, and 12e are shown in the drawing. The nine elements of patch 12a are coupled to nine delay lines of the microbeamformer indicated at DL1. Similarly the nine elements of patches 12c and 12e are coupled to the delay lines indicated at DL2 and DL3. The delays imparted by these delay lines are a function of numerous variables such as the size of the array, the element pitch, the spacing and dimensions of the patch, the range of beam steering and focusing, and others. The delay line groups DL1, DL2, and DL3 each delay the signals from the elements of their respective patch to a common time or phase reference for the patch. The nine delayed signals from each group of delay lines are then combined by a respective summer Σ to form a partial sum signal of the array from the patch of elements. Each partial sum signal is put on a separate bus 15a, 15b, and 15c, each of which is coupled to a conductor of the cable 16, which conducts the partial sum signals to the system mainframe. In the system mainframe each partial sum signal is applied to a delay line 22a, 22b, 22c of a channel of the system beamformer 22. These delay lines steer and focus the partial sum signals into a common beam at the output of the system beamformer summer 22s. The fully formed beam is then forwarded to the system image processor for further signal processing and display. While the example of FIG. 2 is shown with 9-element patches, it will be appreciated that a constructed microbeamformer system will often have patches with larger numbers of elements such as 16, 32, 48, or 70 elements or more. The elements of a patch can be adjacent to each other, be spaced apart, or even intermingled in a checkerboard pattern, with "odd" numbered elements combined in one patch and "even" numbered elements combined in another. The patches can be square, rectangular, diamond-shaped, hexagonal, or any other desired shape.

Figure 3:
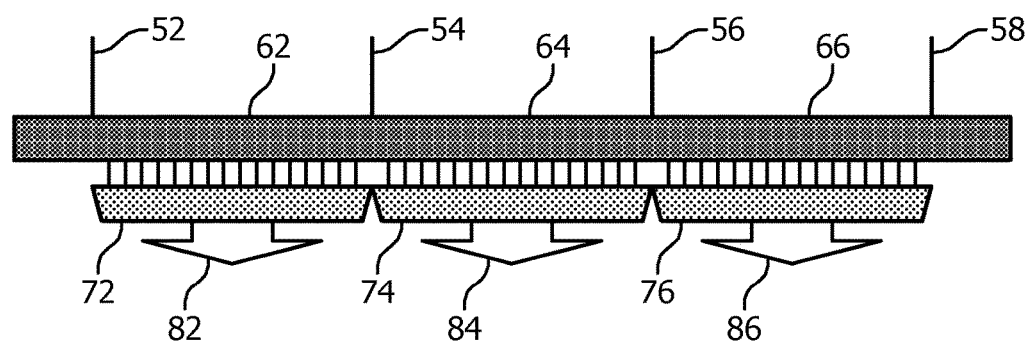
FIG. 3 illustrates three patches of a standard microbeamformer configuration.

FIG. 3 is a simplified illustration of a probe array transducer and microbeamformer of the standard configuration. Lines 52, 54, 56, and 58 indicate boundaries between three patches of a microbeamformer. The dark areas 62, 64, and 66 represent the elements and delay lines of each patch. In this example each patch contains sixteen elements and delay lines. The elements and delay lines of each patch are coupled to a summing node, indicated for the three patches as 72, 74, and 76. A summing node combines the sixteen signals of the elements and delay lines of the patch and produces one beamsum output signal which is coupled to a channel of the system beamformer as indicated by output arrows 82, 84, and 86.

Figure 4:
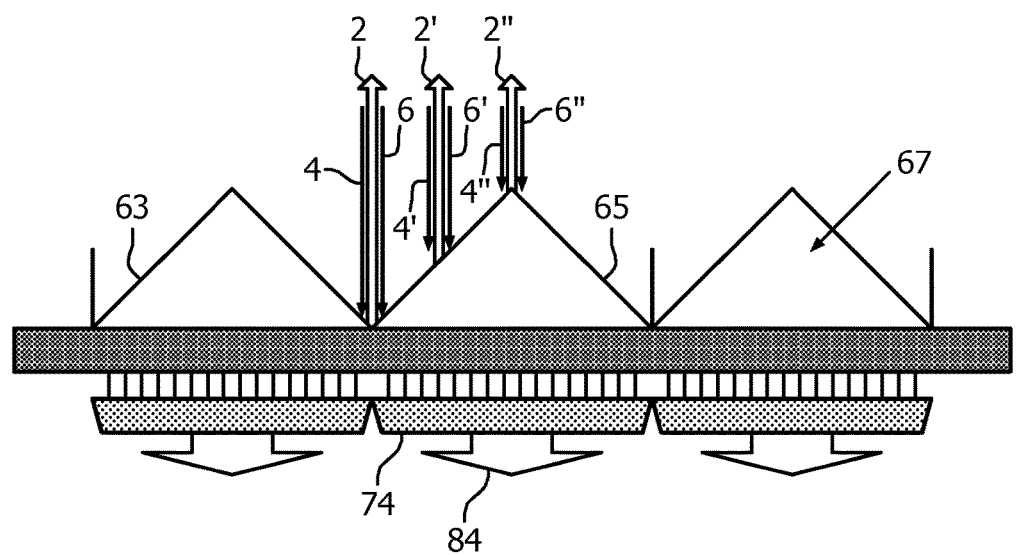
FIG. 4 illustrates the problem of multiline beamforming with a microbeamformer of the standard patch configuration.

With this description, FIG. 4 illustrates the problem encountered when trying to produce multiline receive signals with the microbeamformer of the standard configuration. In FIG. 4 the shaded triangles 63, 65, 67 delineate the sixteen elements and delay lines of three patches, the elements and delay lines of each patch being coupled to a common summing output. Broad upward pointing arrows 2, 2', and 2" indicate three transmit beams which are transmitted at different times and from different points along the array to scan the image field in front of the array. In this example each transmit beam insonifies two multiline positions 4 (4', 4") and 6 (6', 6") located on either side of the center of the transmit beam. Two multilines are then received in response to each transmit beam, which is referred to as 2× multiline. Higher order multiline may also be employed, such as 4×, 8×, or 16× multiline. After a transmit beam 2 is transmitted, echoes are received starting in the near field and are differently delayed and summed in the system beamformer so that receive multilines are steered for reception along the two multiline positions.

It is seen that transmit beam 2" is located at the center of patch 65. When echoes are received by the elements around this patch location to be formed into receive multilines 4" and 6", it is seen that they are, at least in the near field, received by elements of the same patch 65. Thus, signals received in the near field will be delayed and combined into one beamsum signal at output 84 of the patch and coupled to a single channel of the system beamformer, which will apply its delay to the signal. Similarly, the two multiline locations 4' and 6' on either side of transmit beam 2' will have their near field echoes received only by elements of patch 65. This problem does not occur in the instance of transmit beam 2, which is centered at the boundary between patches 63 and 65. Nearfield echoes from multiline locations 4 and 6 on either side of the center of the transmit beam will be received by elements of patches 63 and 65 and coupled to two system beamformer channels where different delays can be applied to the separate beamsum signals. For this particular transmit beam and its multilines there will be no near field artifacts as beam steering of the different multilines can commence in the near field.

Figure 5A:
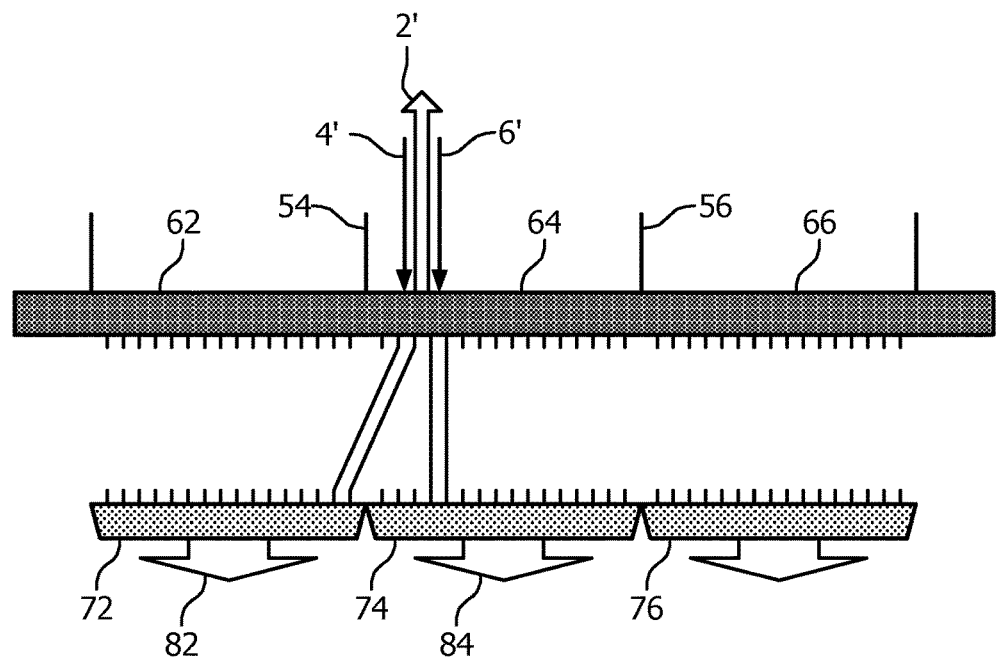
FIGS. 5A-5D illustrate a microbeamformer of the present invention when receiving echoes for multiline formation with an expanding aperture in accordance with the principles of the present invention.

FIGS. 5A-5D illustrate how this near field multiline beam steering problem can be overcome in accordance with the present invention. In FIG. 5A a beam 2' has been transmitted which is centered on patch 64. Two multilines 4' and 6' are to be received on either side of the center of the transmit beam. In the near field echo reception is initially performed by only four elements and delays of patch 64, two to the left of the transmit beam center and two to the right. The two elements to the right of the beam center are coupled to the summing node of patch 64 in their standard configuration. But the two elements to the left of the beam center are coupled to the summing node 72 of the patch 62 to the left of patch 64. The sum of the two received and delayed signals coupled to summing node 74 are produced at the beamsum output 84, and the sum of the two received and delayed signals coupled to summing node 72 are produced at the beamsum output 82. Since these two outputs are coupled to different channels of the system beamformer they can be delayed differently by the system beamformer to produce different multilines, enabling received echo signals to be translated to either side of the center of the transmit beam. To connect the received and delayed signals from the elements to the left of the transmit beam center to the summing node 72 of the adjacent patch 62, a two position switch can be used for each signal path. When the switch is set in its nominal position the signals from the elements are coupled in the normal configuration to the summing node 74 of patch 64. When the switch is set in its second position, the signals are coupled to the summing note 72 of adjacent patch 62.

Figure 5B:
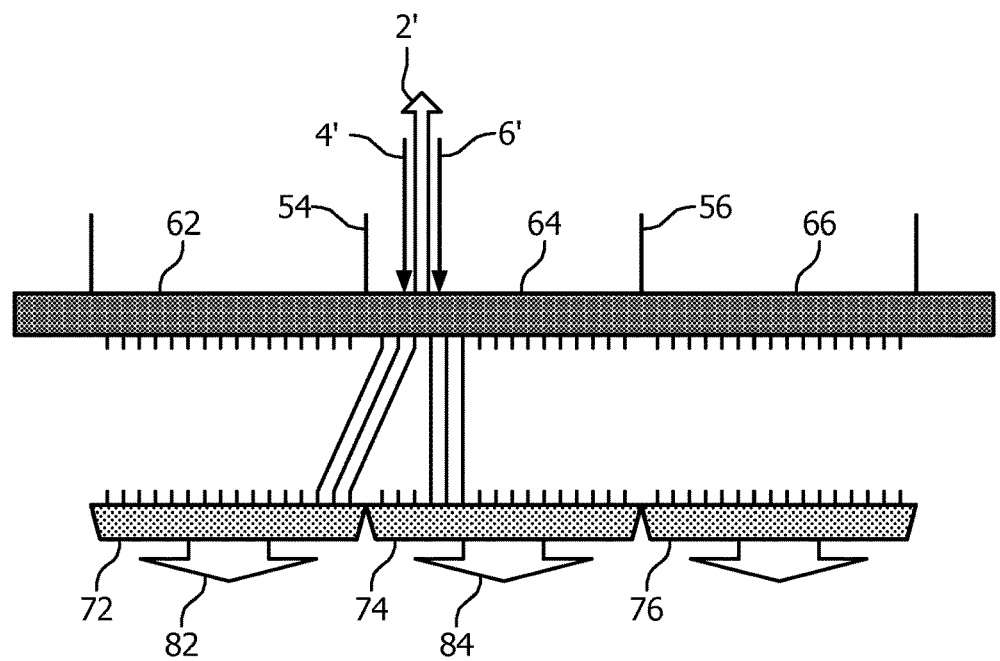
Figure 5C:
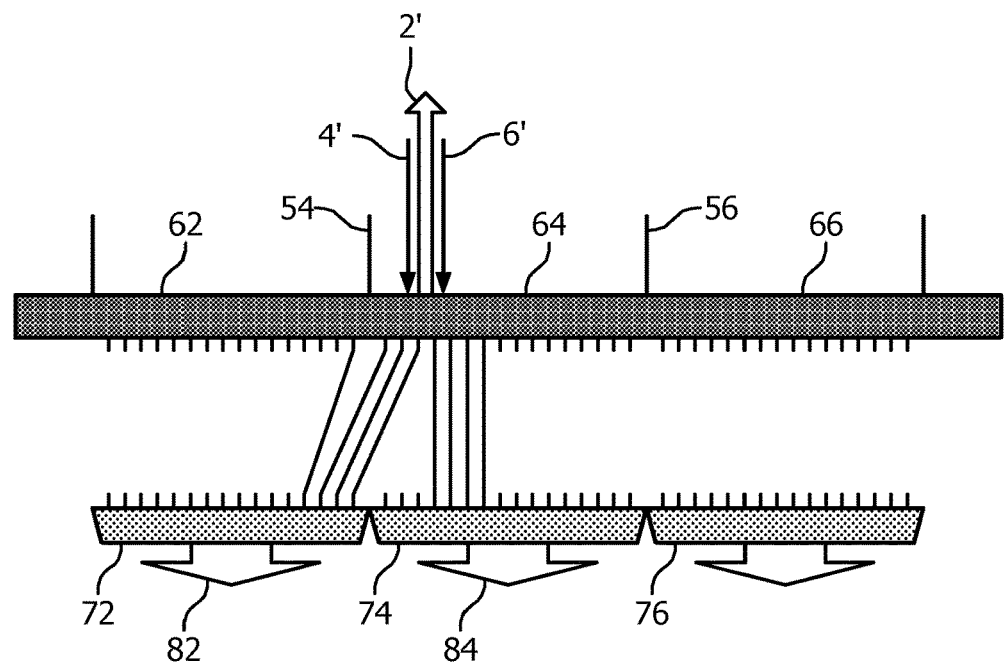
Figure 5D:
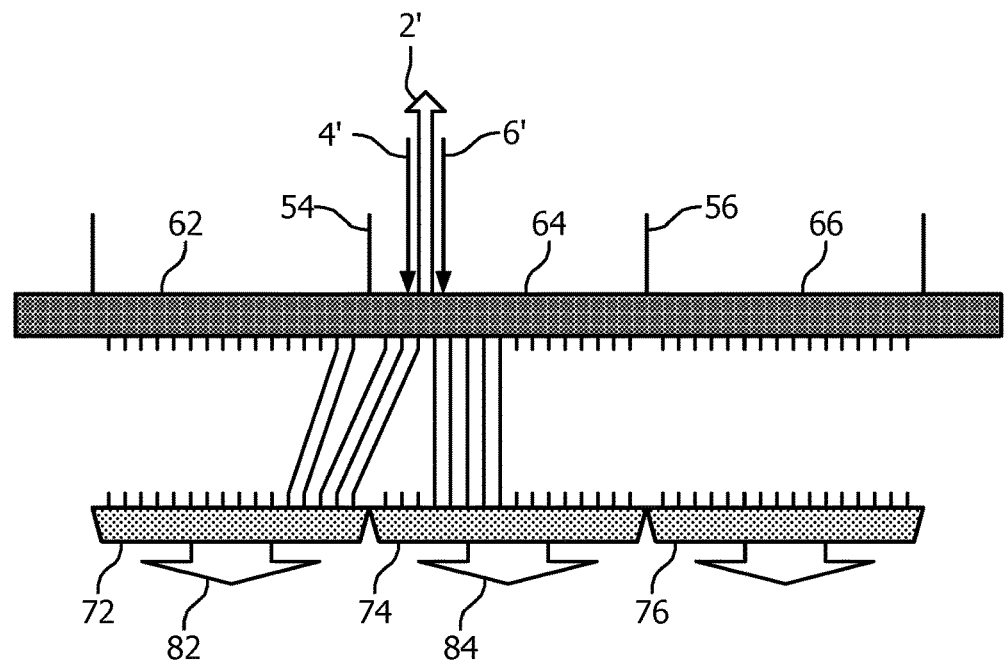

As mentioned previously, the receive aperture of a beam-former system is expanded as echoes are received from greater depths. In this example the aperture is next expanded by adding an additional element on either side of the original four elements as echoes are received from a greater depth. FIG. 5B illustrates that the three elements to the right of the transmit beam center are coupled to the summing node 74 or patch 64, and the three elements to the left of the transmit beam center are coupled to summing node 72 of patch 62. The two beamsums are coupled to two channels of the system beamformer from the outputs 82 and 84. This expansion of the aperture continues at greater depths with the addition of one and then another element of either side of the transmit beam center as shown in FIGS. 5C and 5D. As in the beginning of this example, elements and delays to the left of the beam center are all coupled to summing node 72 and beamsum output 82 of the adjacent patch 72 and elements and delays to the right of the beam center are all coupled to summing node 74 and beamsum output 84 of patch 64 of the microbeamformer. The system beamformer is thus able to continuously steer each multiline along the appropriate side of the beam center, even at the shallowest depths of echo reception.

Figure 6:
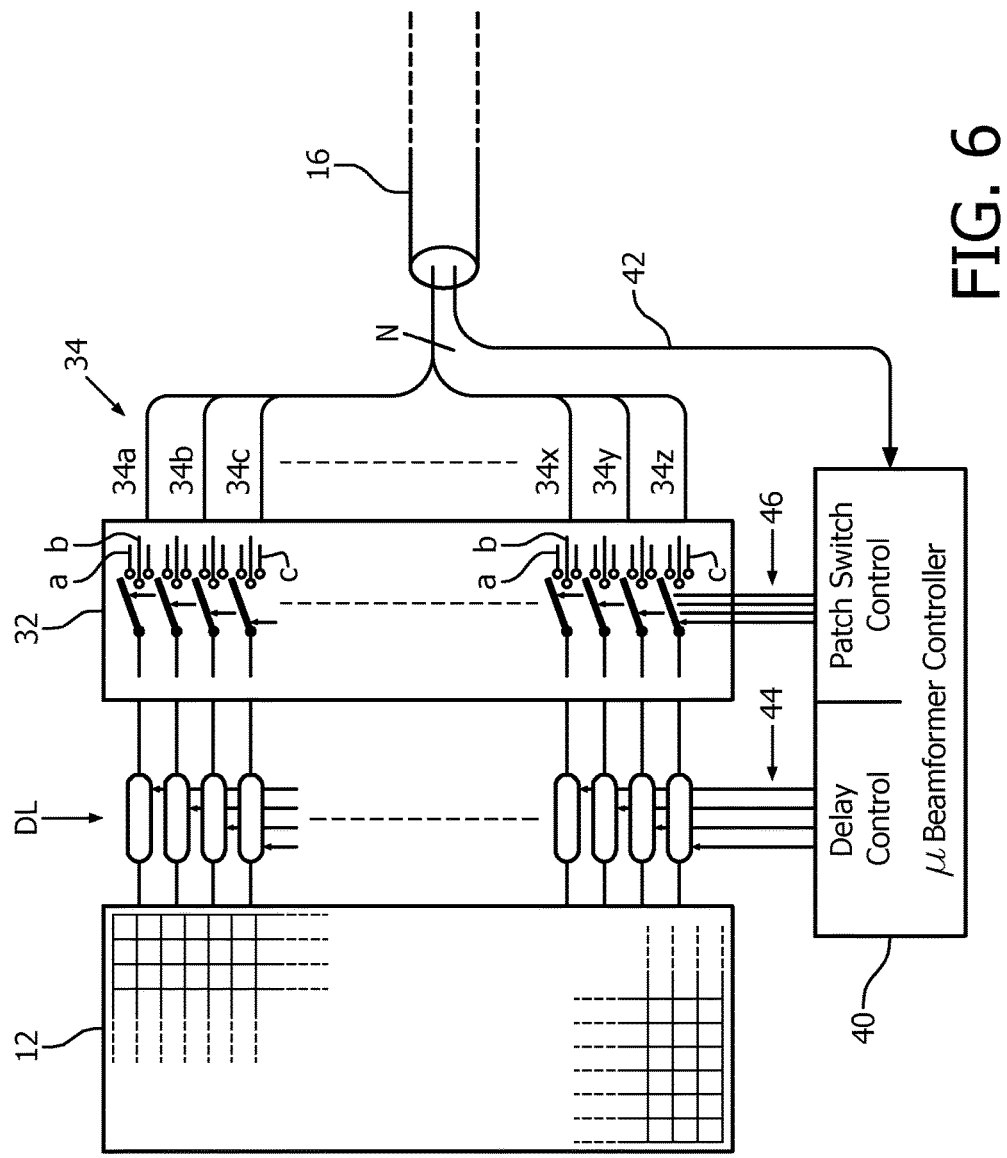
FIG. 6 illustrates in block diagram form a microbeamformer constructed in accordance with the principles of the present invention.

An implementation of the present invention which enables this partitioning of received echo signals is illustrated in block diagram form in FIG. 6. The elements of the array transducer 12 are shown coupled to delays DL of the microbeamformer 14 of the ultrasound probe. A microbeamformer controller 40 controls the magnitudes of the applied delays through a delay control section as indicated by delay control lines 44. The microbeamformer controller receives control signals over one or more lines 42 from the main system. A switch matrix 32 contains switches which are each coupled to receive signals from a respective delay DL. While the switches can be formed as mechanical switches, in a constructed embodiment they are manufactured in semiconductor form as analog passgates. The arm of each switch in this preferred implementation has three possible settings, positions a, b, and c. Position b is the nominal, straight ahead position, coupling an element and delay to its usual summing node. In the previous example this means that the elements and delays of patch 64 are coupled to summing node 74 and output 84 when the switches are set in this position. Setting a switch to the a position couples its element and delay to the patch on one side of the straight-ahead patch, and setting a switch to the c position couples its element and delay to the patch on the other side. For instance, when a switch of patch 64 is set to position a, the signals of the switches are coupled to summing node 72 of the patch 62 to the left, and when the switch is set to position c, its signals are coupled to summing node 76 of the patch 66 to the right. In the implementation of FIG. 6, setting all of the switches shown at the top of the switch matrix to the b position would couple their delays DL to output line 34*b* of the microbeamformer, which is coupled over a line of cable 16 to one channel of the system microbeamformer. When all of these switches are coupled to output line 34*b*, all of their signals will be combined into one beamsum signal on that line. Similarly, when the switches at the top are set in position a their signals will be combined on output line 34*a* and coupled over the cable to another channel of the system beamformer, and when the switches are set in the c position their signals will be combined on output line 34*c* and coupled over the cable to a third channel of the system beamformer. The use of three-position switches in switch matrix 32, which provides the capability to direct a signal to either of two adjacent patches provides greater flexibility in partial beamsum formation as will be illustrated by the examples described below. It will be appreciated that this control setting, enabled by patch switch control signals on lines 46 from the microbeamformer controller, is possible so long as a patch has other patches on both sides. At the ends of the array a patch will have no patch beyond the end of the patch and this control cannot be fully performed. Except for this boundary condition, this control prevails over the rest of the length of the array and its patches.

Figure 7:
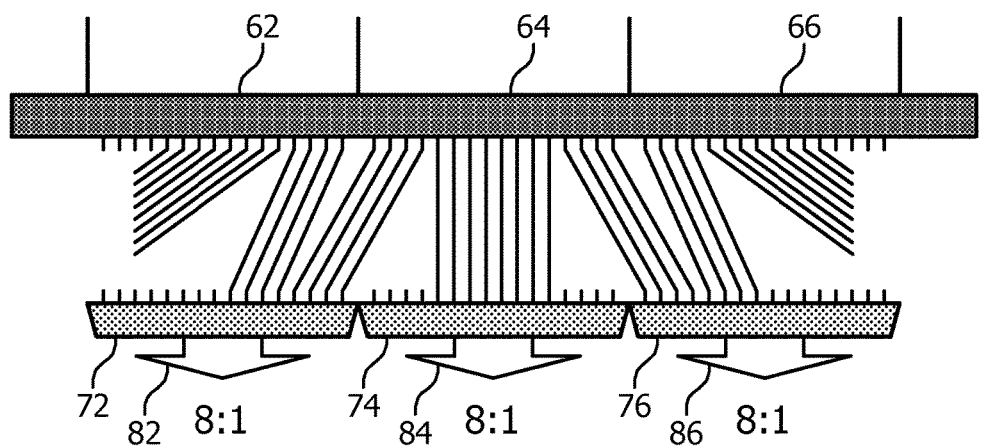
FIG. 7 illustrates a microbeamformer of the present invention when configured for operation with a system beamformer of a greater number of channels.

The ability to couple the signals from an element of a patch to not only its own patch but also to a neighboring patch on either side enables the ability to reconfigure a patch size for different system beamformer configurations. In the previous examples it is seen that each patch nominally is comprised of sixteen elements and the microbeamformer thus produces 16:1 beamsums from the nominal patch sizes. For instance, if the probe is operated with a system beamformer of twice the number of channels, advantage can be taken of the increased number of channels by switching to 8:1 beamsums as shown in FIG. 7. In this example it is seen that eight of the elements and delays of the middle patch 64 are coupled to the summing node 74 and output 84 of the patch. Four of the elements and delays of the patch are coupled to summing node 72 of the patch 62 to the left and its output 82, along with four elements and delays of patch 62. Similarly, another four of the elements and delays of patch 64 are coupled to summing node 76 of the patch 66 to the right and its output 86, along with four elements and delays of patch 66. It is seen that this switching of the signals from the array elements produces 8:1 sum signals and a redefinition of the aperture of the probe.

Figure 8:
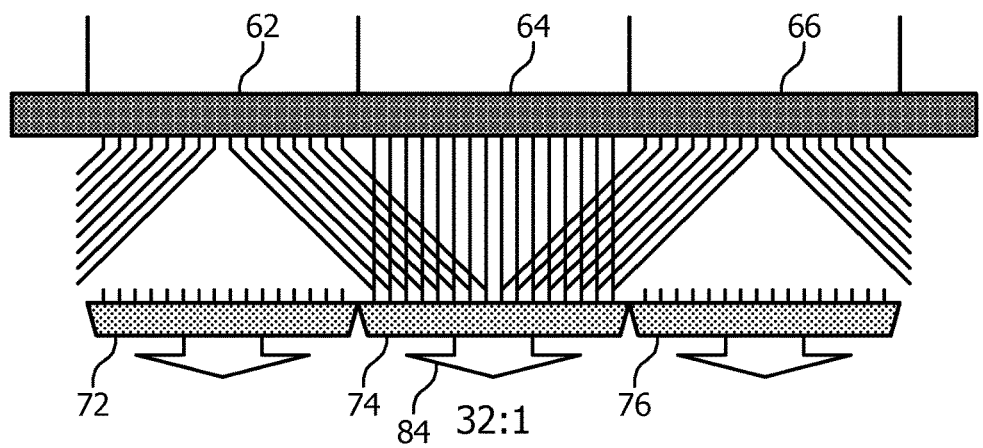
FIG. 8 illustrates a microbeamformer of the present invention when configured for operation with a system beamformer of a fewer number of channels.

The arrangement of FIG. 8 accommodates a situation of a decreased number of system beamformer channels. In this example a system beamformer of only half the number of channels as in the first example is available. The number of signals processed by a system beamformer channel can then be doubled by setting the switches to couple signals as shown in this example. All of the elements and delays of patch 64 are set to their nominal b position, coupling all of their signals to the summing node 74 and the output 84 of the patch. Additionally, eight elements and delays of the neighboring patch 62 are also coupled to summing node 74 by setting their switches to the c position, and eight elements and delays of the other neighboring patch 66 are coupled to summing node 74 by setting their switches to the a position. A 32:1 beamsum signal is thus produced at microbeamformer output 84 and coupled to a system beamformer channel, which now operates with larger patch sizes in the probe.

What is claimed is:

1. An ultrasonic transducer probe and system comprising:
    an array of transducer elements configured as a plurality of adjacent patches of transducer elements, wherein the array of transducer elements is operable to transmit a beam centered on a given patch;
    a microbeamformer coupled to the transducer elements of the array comprising:
        a plurality of controllable delays coupled to elements of the array to produce delayed echo signals;
        a plurality of controllable switches, wherein each of the plurality of controllable switches is individually coupled to a respective one of the plurality of controllable delays to direct the respective delayed echo signal to a selected one of a summing node of the given patch, a summing node of a second patch adjacent to the given patch, and a summing node of a third patch adjacent to the given patch on an opposite side of the given patch; and
        a plurality of microbeamformer outputs, each of the plurality of microbeamformer outputs coupled to at least one of the summing nodes;
    a microbeamformer controller coupled to the microbeamformer and configured to:

control a first plurality of the plurality of controllable switches to direct signals from elements on a first side of the beam center to the summing node of the given patch; and
        control a second plurality of the plurality of controllable switches to direct signals from elements on a second side of the beam center to the summing node of the second patch or the third patch; and
    a system beamformer having a plurality of channels, each of the plurality of channels being coupled to receive a partial beamsum signal from at least one of the plurality of microbeamformer outputs, wherein the system beamformer is configured to process beamsum signals received from the patches to form multiline signals.

2. The ultrasonic transducer probe and system of claim 1, wherein the array of transducer elements and the microbeamformer are located in the transducer probe, and the system beamformer is located in the ultrasonic system.

3. The ultrasonic transducer probe and system of claim 2, wherein the microbeamformer controller further controls the controllable delays.

4. The ultrasonic transducer probe and system of claim 2, wherein the array of transducer elements further comprises a two dimensional array of transducer elements.

5. The ultrasonic transducer probe and system of claim 2, wherein the array of transducer elements further comprises a one dimensional array of transducer elements.

6. The ultrasonic transducer probe and system of claim 1, wherein the summing nodes further comprise microbeamformer output lines.

7. The ultrasonic transducer probe and system of claim 1, wherein the summing nodes further comprise microbeamformer output buses.

8. The ultrasonic transducer probe and system of claim 1, wherein the system beamformer is further configured to steer received echo signals to be received along multilines located on either side of the transmit beam center.

9. The ultrasonic transducer probe and system of claim 1, wherein each patch has a nominal number of transducer elements;
    wherein a first plurality of delayed echo signals of the given patch are directed to the summing node of the given patch;
    wherein a second plurality of delayed echo signals of the given patch are coupled to the summing node of the second patch; and
    wherein a third plurality of delayed echo signals of the given patch are coupled to the summing node of the third patch,
    wherein the system beamformer is configured to operate with patch sizes less than the nominal number of transducer elements.

10. The ultrasonic transducer probe and system of claim 9, wherein the nominal number of transducer elements is sixteen.

11. The ultrasonic transducer probe and system of claim 10, wherein the patch sizes less than the nominal number are eight transducer elements.

12. The ultrasonic transducer probe and system of claim 1, wherein each patch has a nominal number of transducer elements;
    wherein a plurality of delayed echo signals of the given patch are directed to the summing node of the given patch;
    wherein a plurality of delayed echo signals of the second patch are coupled to the summing node of the given patch; and wherein a plurality of delayed echo signals of the third patch are coupled to the summing node of the given patch, wherein the system beamformer is configured to operate with patch sizes greater than the nominal number of transducer elements.

13. The ultrasonic transducer probe and system of claim 12, wherein the nominal number of transducer elements is sixteen.

14. The ultrasonic transducer probe and system of claim 12, wherein the patch sizes greater than the nominal number are thirty-two transducer element patches.

* * * * *